United States Patent [19]

Smith et al.

[11] Patent Number: 5,443,821

[45] Date of Patent: Aug. 22, 1995

[54] ALKOXYLATED COMPOUNDS AND THEIR USE IN COSMETIC STICK FORMULATIONS

[75] Inventors: Ronald J. Smith, River Vale; Steele Elmi, Hawthorne, both of N.J.

[73] Assignee: Application Chemicals, Inc., Glen Rock, N.J.

[21] Appl. No.: 974,161

[22] Filed: Nov. 10, 1992

Related U.S. Application Data

[62] Division of Ser. No. 845,680, Mar. 4, 1992, Pat. No. 5,258,136.

[51] Int. Cl.$^6$ .......................... A61K 7/32; A61K 7/42; C11D 3/48; C11D 9/50
[52] U.S. Cl. ........................... 424/65; 252/106; 252/107; 424/DIG. 5; 424/DIG. 10; 424/DIG. 13; 424/59; 424/60; 424/69; 512/4; 514/773
[58] Field of Search ................ 424/DIG. 5, 65, 59, 424/63; 514/944

[56] References Cited

U.S. PATENT DOCUMENTS

| | | | |
|---|---|---|---|
| 2,213,477 | 9/1940 | Steindorff et al. | 260/613 |
| 2,465,470 | 3/1949 | Omohundro et al. | 167/42 |
| 2,593,112 | 5/1952 | Cross et al. | 260/613 |
| 2,875,153 | 2/1959 | Dalton | 252/132 |
| 3,226,352 | 12/1965 | Helin et al. | 260/29.6 |
| 3,562,167 | 2/1971 | Kamen et al. | 252/121 |
| 3,839,212 | 10/1974 | McCoy | 252/52 |
| 4,226,889 | 10/1980 | Yuhas | 424/59 |
| 4,252,789 | 2/1981 | Broad | 424/65 |
| 4,265,878 | 5/1981 | Keil | 424/66 |
| 4,268,498 | 5/1981 | Gedeon et al. | 424/65 |
| 4,322,400 | 3/1982 | Yunas | 424/59 |
| 4,504,465 | 3/1985 | Sampson | 424/65 |
| 4,606,837 | 8/1986 | McEntire et al. | 252/73 |
| 4,617,185 | 10/1986 | DiPietro | 424/65 |
| 4,759,924 | 7/1988 | Luebbe et al. | 424/42 |
| 4,842,762 | 1/1989 | Sabol et al. | 252/109 |
| 4,954,333 | 9/1990 | Ward | 424/66 |
| 5,120,541 | 6/1992 | McCaulay | 424/401 |
| 5,128,123 | 7/1992 | Brewster et al. | 424/65 |
| 5,151,269 | 9/1992 | Greenshields et al. | 424/65 |
| 5,198,218 | 3/1993 | Kuznitz et al. | 424/65 |
| 5,258,136 | 11/1993 | Smith et al. | 514/944 |

*Primary Examiner*—Dale R. Ore
*Attorney, Agent, or Firm*—Weingram & Zall

[57] ABSTRACT

Novel phenol compounds of the formula:

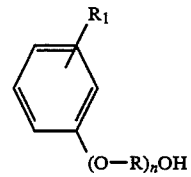

FORMULA A wherein $R_1$ is an alkyl substituent of from 8 to 18 carbon atoms, R is an ethyl or propyl substituent, and n is from about 50 to 200.

These compounds as well as certain other similarly alkoxylated compounds, for example, a compound of the formula:

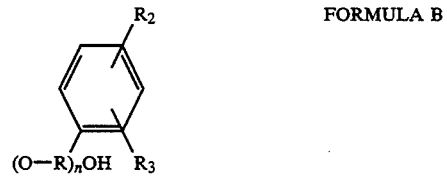

FORMULA B wherein $R_2$ and $R_3$ are each, independently an alkyl substituent of 8 to 15 carbon atoms, R is an ethyl or propyl substituent, and n is from about 50 to 200, may be used in sodium stearate based stick gels to enhance transparency, minimize syneresis and/or increase the setting point of the gel.

11 Claims, No Drawings

ALKOXYLATED COMPOUNDS AND THEIR USE IN COSMETIC STICK FORMULATIONS

This is a divisional of application(s) Ser. No. 07/845,680, filed on Mar. 4, 1992, now U.S. Pat. No. 5,258,136.

BACKGROUND OF THE INVENTION

1. Field of the Invention

This invention relates to certain alkoxylated compounds, e.g. alkoxylated fatty alcohols, fatty acids, fatty esters and phenols, and especially novel substituted alkoxylated phenols, and their use in cosmetic gel formulations, and in particular, their use in novel sodium stearate gel stick formulations.

2. Prior Art

It has been found that prior art gel compositions, particularly sodium stearate gel stick formulations, designated as clear or translucent do not have the degree of clarity desirable in such products. Moreover, many of the prior art products tend to become cloudy or hazy after standing for a period of time. Typically the haziness becomes progressively worse, so that after about a month the product is cloudy and can be said to have little or no transparency. Since products such as these are stored for one or more months subsequent to manufacture, the length of time a product retains a major portion of its transparency is an important characteristic. Numerous patents exist relating to sodium stearate stick formulations and alkoxylated compounds, such as alkoxylated phenols, and their use. See for example the following:

| U.S. PAT. NO. | INVENTOR |
| --- | --- |
| 2,213,477 | Steindorff et al |
| 2,465,470 | Omohundro et al |
| 2,593,112 | Cross et al |
| 3,226,352 | Helin et al |
| 3,839,212 | McCoy |
| 4,226,889 | Yuhas |
| 4,252,789 | Broad |
| 4,268,498 | Gedeon et al |
| 4,322,400 | Yuhas |
| 4,504,465 | Sampson |
| 4,606,837 | McEntire et al |
| 4,617,185 | DiPietro |
| 4,842,762 | Sabol et al |
| 4,954,333 | Ward |

More specifically:

Steindorff et al, U.S. Pat. No. 2,213,477 discloses parasubstituted ethoxylated phenols having from 6 to 25 ethoxy groups and from 8 to 20 carbons in the alkyl substituent. The compounds are described as useful as wetting agents, softening agents or auxiliary agents for finishing textiles as well as other uses.

Cross et al, U.S. Pat. No. 2,593,112 discloses di-substituted ethoxylated phenols having from 10 to 25 ethoxy groups. Hydrophobic groups containing 8 and 12 carbons are disclosed. The compounds are described as being useful as wetting agents.

Helin et al, U.S. Pat. No. 3,226,352 discloses parasubstituted ethoxylated phenols having from 7 to 15 ethoxy groups. A hydrophobic group containing 9 carbons is disclosed.

McCoy, U.S. Pat. No. 3,839,212 discloses a nonyl ethoxylated phenol having 30 ethoxy groups. McCoy is directed to a process for converting polymeric alkoxylated substrates containing from 1 to 50 alkoxylated groups that are normally insoluble in mineral oil to compounds that are soluble in mineral oil.

McEntire et al, U.S. Pat. No. 4,606,837 discloses water-glycol fluids made from polyoxyalkylene thickeners that employ dinonylphenol that is ethoxylated. A preferred range of ethoxylation is 40:1 to 500:1 and dodecylphenol may be ethoxylated.

Omohundro et al, U.S. Pat. No. 2,465,470 discloses an insect repellent stick that employs a sodium stearate gel.

Yuhas, U.S. Pat. No. 4,226,1189 discloses a sodium stearate based stick that includes polyethylene glycol additives. Yuhas '889 is directed to a stick composition consisting essentially of (a) 100 parts by weight of water and from about 1 to about 30 parts by weight of sodium stearate and (b) an active ingredient in the range of from about 0.05 to about 50 weight percent of the total weight of the composition.

Yuhas, U.S. Pat. No. 4,322,400 discloses a cosmetic stick that is sodium stearate based and has polyethylene glycol and sodium chloride, which reduces syneresis.

Gedeon et al, U.S. Pat. No. 4,268,498 discloses a clear cosmetic stick comprised of a number of ingredients, none of which includes sodium stearate or a hydrophobe substituted alkoxylated phenol. At column 1, lines 8-15, there is a disclosure that sodium stearate based sticks get hazy and cloudy.

DiPietro, U.S. Pat. No. 4,617,185 discloses deodorant sticks that employ sodium stearate and a condensation product having a formula set out at column 6, lines 20-23 which includes ethoxy and propoxy groups.

Sabol et al, U.S. Pat. No. 4,842,762 discloses a laundry soil and stain remover in applicator stick form. Formulations are set out in Examples 1 and 4 in which Donylphenol ethoxylate and stearic acid are employed. In Example 4, sodium ions are also present.

Broad, U.S. Pat. No. 4,252,789 is of interest for its disclosure of deodorant sticks that include a mixture of sodium stearate and sodium palmitate and an ethoxylated polyethylene imine.

Sampson, U.S. Pat. No. 4,504,465 is of interest for its disclosure of cosmetic sticks that have ethylene oxide and/or propylene oxide condensation products.

Ward, U.S. Pat. No. 4,954,333 is of interest for its disclosure of transparent antiperspirant stick compositions that are not sodium stearate based.

Additionally, European Patent Application No. 911052587 (Publication No. 0 450 597A2) describes a gel stick which incorporates a water dispersible emollient that is a polyoxyethylene ether of a branched chain fatty alcohol, the fatty alcohol having from 8 to about 22 carbons and the average number of ethylene glycol ether units being from about 1 to 6. The gel stick composition has enhanced transparency to the transmission of light.

None of the aforedescribed references teach or suggest the novel class of substituted alkoxylated phenols described and claimed herein. Additionally, none of the aforedescribed patents teach or suggest the use of these compounds and other similarly alkoxylated compounds in sodium stearate stick formulations and the advantages derived therefrom.

OBJECTS AND SUMMARY OF THE INVENTION

It is an object of the present invention to provide an improved stable sodium stearate cosmetic gel.

It is another object of this invention to provide sodium stearate gel sticks suitable as deodorant sticks fragrance sticks, lipsticks, soap bars, and the like.

Another object of this invention is to produce a sodium stearate gel having a high setting temperature which assists in preventing shrinkage of the gel.

Still another object of this invention is to make available certain new alkoxylated phenols.

Another object of this invention is to increase the solubility of fragrance ingredients in sodium stearate gels while maintaining a clear stick.

A further object of this invention is to provide a sodium stearate gel stick which requires less sodium stearate and forms a transparent stick.

The foregoing objects of this invention are achieved by incorporating in a sodium stearate gel a compound of the formula:

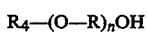

$$R_4-(O-R)_nOH$$

wherein $R_4$ is (a) lanolin, (b) mono- and di-glycerides of $C_{12}$ to $C_{22}$ fatty acids, or (c) $C_{12}$ to $C_{22}$ fatty acids; and R is an ethyl or propyl substituent and n is from 50 to 200.

The foregoing objects of this invention are also achieved by incorporating in a sodium stearate gel novel alkoxylated phenols of the formula:

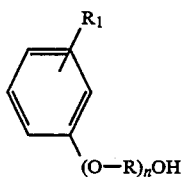

Formula A $(O-R)_nOH$ wherein $R_1$ is an alkyl substituent from 8 to 18 carbon atoms, R is an ethyl ($-C_2H_4-$) or propyl substituent ($-C_3H_6-$) and n may range from 50 to 200. Preferably n is about 200, $R_1$ is about 15 carbon atoms and the O—R or O-alkyl group is $OC_2H_4$.

Other preferred compounds for such use are for example:

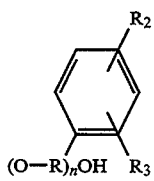

Formula B $(O-R)_nOH$  $R_3$ wherein $R_2$ and $R_3$ are each, independently an alkyl substituent of 8 to 15 carbon atoms, preferably a linear alkyl of 9 carbon atoms (nonyl), R is an ethyl or propyl substituent, preferably ethyl and n is from 50 to 200, preferably about 150.

All of the foregoing similarly alkoxylated compounds can be used to prepare stick formulations containing sodium stearate, for example, deodorant sticks, perfume sticks, clear soap, and fragrance sticks.

The use of the foregoing compounds provides for enhanced transparency to sodium stearate gel sticks as opposed to cloudy translucent sticks. The addition of up to about 1 to 8 parts per hundred of the aforedescribed alkoxylated compounds enhances transparency of the gel, minimizes the "syneresis" effect upon storing the final gel sticks at low or high temperature, and also increases the setting point of the gel composition.

DETAILED DESCRIPTION OF THE INVENTION

The gel compositions of the present invention are transparent to the transmission of light. "Transparent" generally means that sufficient light passes through the gel to enable an observer to see through the gel, without difficulty, an image, e.g. lettering. Generally, gel sticks in accordance with the present invention will transmit more than 40% of the light passed therethrough. Further, the gels of the present invention remain transparent for a reasonable period of time, typically at least about one month at room temperature preferably for at least three months at room temperature.

More specifically, the terminology "transparent" may refer to a standard described by F. W. Wells in Soap and Chemical Specialties, Vol. XXI, No. 6 and No. 7 June and July 1955 which provides a criteria for transparency (in actuality translucency). A product, e.g. sodium stearate gel, in order to be considered transparent, i.e. translucent, must permit bold faced type of about 14 point size to be read easily through a quarter-inch section of the product. Other methods, for example "translucency voltage", have been employed to evaluate the transparency and translucency of soaps, see for example U.S. Pat. No. 2,970,116 to Kelly et al, incorporated herein by reference. In actuality, transparency is the limit of translucency wherein no attenuation or loss of transmission occurs, and images viewed through a "transparent" material will appear as if the material were not there at all.

It is believed that the alkoxylated substituent of the compounds used herein serves to solubilize the sodium stearate and prevent crystallization. Further, as the number of alkoxy groups increases, the set-up temperatures of the gel also increases. Still further, the sodium stearate sticks of the present invention do not exhibit syneresis, set up at higher temperatures than similar gels, and maintain truer colors for longer periods of time. Sodium stearate stick formulations, and in particular sodium stearate-propylene glycol/polyethylene glycol stick formulations, are well known in the art, see for example U.S. Pat. No. 4,226,889 to Yuhas, incorporated herein by reference. Compounds which can be incorporated into sodium stearate stick formulations alkoxylated compounds of the formula:

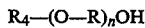

$$R_4-(O-R)_nOH$$

wherein $R_4$ is (a) lanolin, (b) mono- and di-glycerides of to $C_{22}$ fatty acids, or (c) a $_{12}$ to $C_{22}$ fatty acid; and R is an ethyl or propyl substituent and n is from 50 to 200. More specifically:

PEG-50 Lanolin
PEG-75 Lanolin
PEG-100 Lanolin
PPG-12 PEG-65 Lanolin
PEG-78 Glyceryl Stearate PEG-78 Glyceryl Cocoate
PEG-50 Castor Oil
PEG-100 Castor Oil
PEG-200 Castor Oil
PEG-50 Stearate
PEG-100 Stearate
PEG-150 Stearate
PEG-50 Laurate
PEG-100 Laurate
PEG-200 Laurate Additional compounds which can be incorporated into such stick formulations are the novel alkoxylated phenols of the following formula:

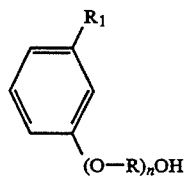

FORMULA A$^1$ wherein $R_1$ is an alkyl substituent of from 8 to 18 carbon atoms, R is an ethyl or propyl substituent, and n is from about 50 to 200. More specifically:
POE-50 Octyl Phenyl Ether
POE-100 Octyl Phenyl Ether
POE-150 Octyl Phenyl Ether
POE-200 Octyl Phenyl Ether
POE-50 Nonyl Phenyl Ether
POE-100 Nonyl Phenyl Ether
POE-150 Nonyl Phenyl Ether
POE-200 Nonyl Phenyl Ether
POE-50 Dodecyl Phenyl Ether
POE-100 Dodecyl Phenyl Ether
POE-150 Dodecyl Phenyl Ether
POE-200 Dodecyl Phenyl Ether
PPG-30 POE-70 Nonyl Phenyl Ether
POE-100 m-Pentadecyl Phenyl Ether
POE-150 m-Pentadecyl Phenyl Ether
POE-200 m-Pentadecyl Phenyl Ether
PPG-20 POE-150 m-Pentadecyl Phenyl Ether Additional alkoxylate phenols which can be incorporated in such stick formulations are:

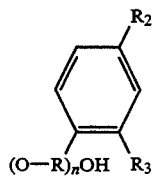

FORMULA B$^1$ wherein $R_2$ and $R_3$ are each, independently, an alkyl substituent of 8 to 15 carbon atoms, R is an ethyl or propyl substituent, and n is from about 50 to 200. More specifically:
POE-50 Dinonyl Phenyl Ether
POE-100 Dinonyl Phenyl Ether
POE-150 Dinonyl Phenyl Ether
POE-200 Dinonyl Phenyl Ether
PPG-40 POE-150 Dinonyl Phenyl Ether Of these latter compounds Igepal DM 970 marketed by the General Aniline and Film Corporation is preferred. DM 970 is an ortho-para-nonyl ethoxylated phenol having 150 ethoxy groups. Other such phenols having other hydrophobic groups such as $C_8$-$C_{15}$ for instance, are also useful, such as Sulfine$^R$ WLL supplied by Finetex, Inc., but Igepal DM 970 is preferred.

A propoxy group may replace the ethoxy group in the alkoxylated hydrophobe. Mixtures of ethoxy-propoxy groups on the alkoxylated hydrophobe may also be useful.

The present substituted alkoxylated phenols are prepared by reacting the substituted phenol with an alkaline oxide in the presence of an alkaline catalyst as is well-known in the art. The number of ethoxy groups, i.e. about 50–200 or more are added in this preparation.

Preferably, for example, the alkoxylated phenols are added to an aqueous sodium stearate gel stick formula in amounts of about one to eight parts per hundred, preferably about two to four parts per hundred to produce the desired transparent gel stick. The amount of sodium stearate in the gel is well-known in the art, e.g. about 1–30 parts by weight per 100 parts of water, about 8 parts of sodium stearate being preferred. Of course, the optimum proportion of sodium stearate to water in any particular instance will depend upon the nature of the other ingredients of the cosmetic stick composition. Nonetheless, most useful compositions will have proportions of sodium stearate to water within the above ranges.

Another essential ingredient of the cosmetic stick composition is an "active ingredient", by which is meant an ingredient which is desired to deposit on the skin of a human being. Such active ingredients can include biologically active materials such as bacteriostats and fungistats, pigments and dyes or other colorants, perfumes, emollients, ultraviolet absorbers or "sun screens", and talc. Of course, any active ingredient must be stable in the aqueous alkaline environment provided by the sodium stearate-water vehicle. Depending upon the intended use of the cosmetic stick composition, the amount of the "active ingredient" can vary from as little as 0.05 weight percent or less up to 50 weight percent or more of the total weight of the composition. Two or more active substances may also be present. For example, a talc stick can also include a bacteriostat and/or a fungistat for use as a medicated powder stick, for example a foot powder stick, or it can contain a pigment for use as a pigmented talc stick.

Still other components of the cosmetic stick are odorants and colorants, which are primarily intended to impart an odor or fragrance to the stick composition. Ordinarily, such additives will comprise from about 0.1 to about 1 weight percent of the cosmetic stick compositions.

The amount of active ingredients, when employed, should be balanced with the amount of sodium stearate so that the setting point of the composition is in the range of from about 65° C. to about 75° C. and preferably is from about 70° C. to about 75° C., and optimally is about 72° C. The specific amounts of active ingredients and sodium stearate which may be used in any specific composition are readily determined through routine experimentation.

The sodium stearate stick composition is formed by mixing the ingredients at elevated temperatures sufficient to form a liquid solution or suspension, ordinarily about 70° C. to about 85° C., pouring the liquid into a mold or dispensing container and allowing it to cool and set. As indicated previously, the use of the alkoxylated phenols increase the set temperature. In some cases, a period of several hours or even days may be required before the cosmetic stick composition is completely solidified. It is preferred that the water and sodium stearate, and optionally the other liquid or liquefiable ingredients, be first mixed to form a clear solution, and the solid ingredients, be first mixed to form a clear solution, and the solid ingredients such as talc or pigments are then added. The mixture is then partially cooled, at which time volatile components, such as perfume oils, are added, and then final cooling is effected.

The remainder of the gel stick formula, as known in the art, includes a glycol such as propylene glycol, butylene glycol, glycerine, polyethylene glycol and the like, as known in the art in concentrations of about 25–80 parts and preferably about 50–70 parts, and the rest water. Other ingredients such as urea, a solubilizer, may be used in the present gel formula.

It is an advantage of the present invention to use stearic acid and neutralize it in situ to produce the sodium stearate in the present gel formula. Stearic acid is considerably less expensive and thus a more inexpensive gel stick may be made using the stearic acid rather than preformed sodium stearate.

When the cosmetic stick composition is subjected to temperature extremes, e.g. a temperature as low as about 0° to 40° C., or a temperature of about 50° C. or higher, it has been found that liquid exudes from the solid stick. Attempts to prevent such "syneresis" through the use of increased amounts of sodium stearate have not proven to be particularly successful because a hard, waxy composition results. It has been further found, however, that the addition of relatively small amounts of the alkoxylated compounds used in this invention increases the setting point, as well as the rate of setting, of the water-sodium stearate cosmetic stick base. Thus, stick-type cologne compositions which otherwise might be too soft for practical use in a stick-type product, such as deodorant colognes containing high proportions of such compounds, perfume oils, can be formulated into a cosmetic stick composition by the use of such compounds.

It has been found with both the novel and known alkoxylated compounds used in this invention that as the mole level of ethoxylation or propoxylation increases from above 50 to the upper limit of 200, both clarity and the structural integrity of the sodium stearate gel improve.

Further, the larger the hydrophobe on the alkoxylated compound, i.e. $R_1$, $R_2$, $R_3$, $R_4$ herein, the greater the clarification of the sodium stearate gel.

These same principles have been seen to apply, but with a lower degree of success with "substrates" other than phenol. For example most fatty substrates, when ethoxylated, show activity in clarifying sodium stearate/propylene glycol sticks, and with different effects on stick integrity. For example:

a] The alkoxylated esters of lanolin, mono and diglycerides of $C_{12}$ to $C_{22}$ fatty acids described herein give some improvement in clarity, but make overly soft sticks;

b] Alkoxylated fatty acids of $C_{12}$ to $C_{22}$ described herein, such as stearic, give some improvement in clarity, but also make overly soft sticks;

c] The alkoxylated fatty alcohols impart good clarity to such gel sticks, with higher molecular weight alcohols, giving the best results, e.g. Steareth-100, along with good stick integrity; and d] The preferred alkoxylated substituted phenols described herein impart very good clarity and structural integrity to the sticks, with higher molecular weight substituted phenols, e.g. POE[150] dinonyl phenol, POE[200] pentadecyl phenol, being the best.

Numerous type sodium stearate stick gels may be produced, for example deodorant sticks, perfume sticks, sun sticks, lanolin sticks, talc sticks, deodorant cologne sticks, insect repellant sticks, etc.

The following examples are illustrative of the present invention and are not intended to be limiting.

EXAMPLE 1-A

Three gel compositions were prepared containing various proportions of ingredients using Igepal DM 970.

The first composition contained the following ingredients:

| | |
|---|---|
| Na Stearate | 4.0 parts |
| Propylene glycol | 71.0 parts |
| Water | 20.0 parts |
| Igepal DM 970 | 4.0 parts |
| Urea | 1.0 parts |

The above mixture was heated to about 80°–85° C. with stirring and poured into dispensing molds. Gelling commenced at about 70° C. The product had excellent transparency.

EXAMPLE 1-B

This composition contained the following ingredients and prepared as above:

| | |
|---|---|
| Na Stearate | 4.0 parts |
| Propylene glycol | 72.0 parts |
| Water | 20.0 parts |
| Igapal DM 970 | 3.2 parts |
| Urea | 0.8 parts |

Sticks were molded as in "A" above. The product also had excellent transparency.

EXAMPLE 1-C

The following gel formula contained the following ingredients and was prepared as in "A" above:

| | |
|---|---|
| Na Stearate | 4.0 parts |
| Propylene glycol | 73.0 parts |
| Water | 2.0 parts |
| Igepal DM 970 | 2.4 parts |
| Urea | 0.6 parts |

This molded product had excellent transparency.

The products from A, B & C above were allowed to stand for 9 months at room temperature. They showed no shrinkage or syneresis and remained transparent and smooth to the touch.

Other gels were similarly formulated and had the following compositions:

| | | | | | |
|---|---|---|---|---|---|
| Na Stearate | 4% | 4% | 7% | 7% | |
| Propylene Glycol | 72% | 68% | 70.25% | 70.25% | |
| Water | 20% | 20% | 21.42% | 21.42% | |
| Igepal DM 970 | 43% | 8% | 1.0% | 2.0% | |
| Urea | — | — | — | — | |
| Na Stearate | 4% | 4% | 4% | 4% | 4% |
| Propylene Glycol | 71% | 72% | 73% | 65.7% | 58% |
| Water | 20% | 20% | 20% | 27.3% | 35% |

-continued

| | | | | | |
|---|---|---|---|---|---|
| Igepal DM 970 | 4.0% | 3.20% | 2.4% | 2.4% | 2.4% |
| Urea | 1.0% | .8% | .60% | .60% | 0.6% |

EXAMPLE 2
IN-SITU FORMATION OF SODIUM STEARATE

The following mixture was heated to 80° C. to a melt, and poured into molds where it hardened at about 70° C. to a transparent product.

| | |
|---|---|
| Stearic acid | 3.9 parts |
| NaOH (50% soln.) | 1.2 parts |
| Polyethylene glycol | 72.0 parts |
| Water | 18.9 parts |
| Ethoxylated meta-nonyl phenol having 200 ethoxy groups ("PDP-200") | 4.0 parts |

The pH was initially 9.37.

The product was an elegant transparent sodium stearate stick.

EXAMPLE 2-B

The following mixture was prepared similar to Example 2, but without PDP 200.

| | |
|---|---|
| Stearic Acid | 6.847 parts |
| NaOH (50% soln.) | 2.02 parts |
| Polyethylene Glycol | 72.00 parts |
| Water | 19.133 parts | pH initially @ 70° C.=7.82 is adjusted to 9.52. The molded product became cloudy within ½ hour.

EXAMPLE 3
SOAP BAR

| | | |
|---|---|---|
| 1. Na Stearate | 5.0 | parts |
| 2. Polyethylene glycol | 60.1 | parts |
| 3. PDP-200 | 4.0 | parts |
| 4. Monoamide 716 ( ) | 1.0 | parts |
| 5. Water | 17.5 | parts |
| 6. Myristic acid, HY 9514 | 4.5 | parts |
| 7. Lauric acid, HY 9912 | 4.5 | parts |
| 8. NaOH (50% aqueous) | 3.4 | parts |

Components 1 through 4 above were mixed and heated to 80° C. and then cooled to 70° C. with stirring. Components 5 through 8 were mixed and heated to 75° C. with stirring. The two hot mixtures were then combined and heated to about 80° C. with stirring until completely melted and clear. The mixture was poured into soap molds and cooled to produce an elegant transparent soap bar.

EXAMPLE 4
PREPARATION OF OTHER SOAPS USING MYRISTIC AND LAURIC ACIDS

| | A | B |
|---|---|---|
| Sodium Stearate | 4.00 | 5.00 |
| Polyethylene Glycol | 67.68 | 64.70 |
| Water | 18.80 | 18.00 |
| PDP-200 | 4.00 | 4.00 |
| Myristic Acid | 2.00 | 3.00 |
| Lauric Acid | 2.00 | 3.00 |

-continued

| | A | B |
|---|---|---|
| Sodium Hydroxide-50% | 1.52 | 2.30 |

A — Combine and heat sodium stearate and water to 70° C.; combine myristic and lauric acid and heat to 80° C., then add to the sodium stearate solution. To this stirred mixture at 80° C., add the PDP-200 and heat at 80° C. The solution was water-white clear. It was poured into molds at 85° C. The product was clear with soapy character.

B — Same as in A above, but final mixture was heated to 90° C. and yielded a clear water-white solution which was poured into molds at 75° C. Increasing F.A. content to 12.15% from 8.76% resulted in a clearer, less yellowish foamy soap product.

EXAMPLE 5
COMPARISON OF SET-UP TIME WITH AND WITHOUT PPD-200

| | A | B |
|---|---|---|
| Sodium Stearate | 7.0 parts | 4.0 parts |
| PDP - 200 | | 4.0 parts |
| Polyethylene Glycol | 72.0 parts | 72.0 parts |
| Water | 21.00 parts | 20.0 parts |

The above mixtures were stirred to 75° C. and held at 80° C. for about 3-5 minutes then cooled at the same rate to about 70° C. and poured into molds.

Formulation "B" set-up before "A".

| USE OF SULFINE ® WLL (FINETEX) AS THE ALKOXYLATED DINONYL PHENOL | | | | | | |
|---|---|---|---|---|---|---|
| Na Stearate | 4.1 | 5.7 | 4.1 | 4.1 | 4.1 | 4.1 |
| Polyethylene Glycol | 72.0 | 72.0 | 71.0 | 70.0 | 69.0 | 68.0 |
| *Sulfine WLL 70% (Dinonyl phenol ethoxylate) | 5.8 | 3.0 | 5.8 | 5.8 | 5.8 | 5.8 |
| $KHCO_3$ | | | 1.0 | 2.0 | 3.0 | 4.0 |
| Water | 18.1 | 19.3 | 18.1 | 18.1 | 18.1 | 18.1 |

*Sulfine ® WLL - Dinonyl phenol ethoxylate - Finetex (ethoxy group).

Each of the above formulations prepared in the usual manner resulted in clear transparent sticks as in Examples 1-A, B and C.

We claim:

1. A sodium stearate based gel comprising:
   (a) water;
   (b) about 1 to about 30 parts of sodium stearate per 100 parts water (by weight);
   (c) an amount of a phenol compound of the formula:

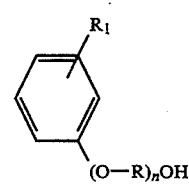

FORMULA A wherein $R_1$ is an alkyl substituent of from 8 to 18 carbon atoms, R is an ethyl or propyl substituent, and n is from about 50 to 200; or

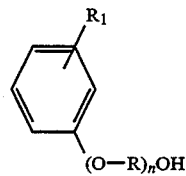

FORMULA A wherein $R_1$ is an alkyl substituent of from 8 to 18 carbon atoms, R is an ethyl or propyl substituent, and n is from about 50 to 200, wherein the amount of phenol is from about 1% to about 8% by weight of the gel; and d) a cosmetically active ingredient intended to be deposited on human skin in the range from about 0.05 to about 50 weight percent of the gel.

5. A sodium stearate based gel comprising:
(a) water;
(b) about 1 to about 30 parts of sodium stearate per 100 parts water (by weight);
(c) an amount of a phenol compound of the formula:

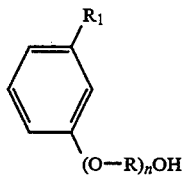

FORMULA $A^1$ wherein $R_1$ is an alkyl substituent of from 8 to 18 carbon atoms, R is an ethyl or propyl substituent, and n is from about 50 to 200, wherein the amount of phenol is from about 1% to about 8% by weight of the gel; and d) a cosmetically active ingredient intended to be deposited on human skin in the range from about 0.05 to about 50 weight percent of the gel.

6. The gel of claim 4, wherein $R_1$ is 15 carbon atoms, R is ethyl and n is about 200.

7. The gel of claim 4, wherein the gel is a transparent deodorant stick.

8. A sodium stearate based gel comprising:
(a) water;
(b) about 1 to about 30 parts of sodium stearate per 100 parts water (by weight):
(c) an amount of a phenol compound of the formula:

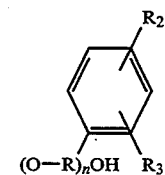

FORMULA B wherein $R_2$ and $R_3$ are each, independently, an alkyl substituent of 8 to 15 carbon atoms, R is an ethyl or propyl substituent, and n is from about 50 to 200, wherein the amount of phenol is from about 1% to about 8% by weight of the gel; and d) a cosmetically active ingredient intended to be deposited on human skin in the range from about 0.05 to about 50 weight percent of the gel.

9. A sodium stearate based gel comprising:

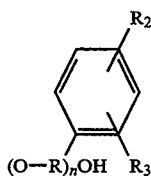

FORMULA B wherein $R_2$ and $R_3$ are each, independently, an alkyl substituent of 8 to 15 carbon atoms, R is an ethyl or propyl substituent, and n is from about 50 to 200, wherein the amount of phenol is from about 1% to about 8% by weight of the gel; and d) a cosmetically active ingredient intended to be deposited on human skin in the range from about 0.05 to about 50 weight percent of the gel.

2. A sodium stearate based gel comprising:
(a) water;
(b) about 1 to about 30 parts of sodium stearate per 100 parts water (by weight);
(c) an amount of a phenol compound of the formula:

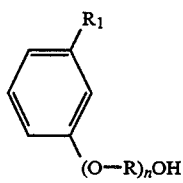

FORMULA $A^1$ wherein $R_1$ is an alkyl substituent of from 8 to 18 carbon atoms, R is an ethyl or propyl substituent, and n is from about 50 to 200; or

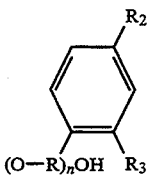

FORMULA $B^1$ wherein $R_2$ and $R_3$ are each, independently, an alkyl substituent of 8 to 15 carbon atoms, R is an ethyl or propyl substituent, and n is from about 50 to 200, wherein the amount of phenol is from about 1% to about 8% by weight of the gel; and d) a cosmetically active ingredient intended to be deposited on human skin in the range from about 0.05 to about 50 weight percent of the gel.

3. The gel of claim 1, wherein the gel is a transparent deodorant stick.

4. A sodium stearate based gel comprising:
(a) water;
(b) about 1 to about 30 parts of sodium stearate per 100 parts water (by weight);
(c) an amount of a phenol compound of the formula;

(a) water;
(b) about 1 to about 30 parts of sodium stearate per 100 parts water (by weight);
(c) an amount of a phenol compound of the formula:

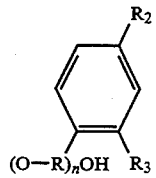  FORMULA B¹ wherein $R_2$ and $R_3$ are each independently, an alkyl substituent of 8 to 15 carbon atoms, R is an ethyl or propyl substituent, and n is from about 50 to 200, wherein the amount of phenol is from about 1% to about 8% by weight of the gel; and d) a cosmetically active ingredient intended to be deposited on human skin in the range from about 0.05 to about 50 weight percent of the gel.

10. The gel of claim 8 wherein $R_2$ and $R_3$ are each 9 carbon atoms, R is ethyl and n is about 150.

11. The gel of claim 8, wherein the gel is a transparent deodorant stick.

* * * * *